| United States Patent [19] | [11] Patent Number: 4,749,801 |
|---|---|
| Beatty et al. | [45] Date of Patent: Jun. 7, 1988 |

[54] [HEXAKIS(PENTENENITRILO)NICKEL II]BIS-[μ-(CYANO) BIS(TRIPHENYLBORANE) (I)], ITS METHOD OF PREPARATION AND ITS USE

[75] Inventors: Richard P. Beatty, LaPlace, La.; John J. Ostermaier, Orange, Tex.

[73] Assignee: E. I. Du Pont de Nemours and Company, Wilmington, Del.

[21] Appl. No.: 870,739

[22] Filed: Jun. 4, 1986

[51] Int. Cl.$^4$ .............................................. C07F 15/04
[52] U.S. Cl. ...................................................... 556/7
[58] Field of Search ............................................. 556/7

[56] References Cited

U.S. PATENT DOCUMENTS

| 3,538,142 | 11/1970 | Drinkard, Jr. ............... | 556/7 X |
|---|---|---|---|
| 3,676,475 | 7/1972 | Drinkard, Jr. ............... | 556/7 |
| 4,082,811 | 4/1978 | Shook, Jr. .................. | 558/335 X |
| 4,328,172 | 5/1982 | Rapoport .................... | 558/335 X |
| 4,347,193 | 8/1982 | Shook, Jr. .................. | 556/7 |
| 4,394,321 | 7/1983 | Cone ........................ | 556/7 |
| 4,416,824 | 11/1983 | Reimer et al. ............... | 556/7 |

OTHER PUBLICATIONS

Chemical Abstracts 98 125452d (1983).
Chemical Abstracts 97 38511h (1982).

*Primary Examiner*—Patrick P. Garvin
*Assistant Examiner*—George R. Fourson
*Attorney, Agent, or Firm*—Earl L. Handley

[57] ABSTRACT

Process for preparing a new compound: [hexakis(pentenenitrilo)nickel II]bis[μ-(cyano)bis(triphenylborane)(I)] which is useful as a promoter in the hydrocyanation of 3 or 4-pentenenitrile.

4 Claims, 3 Drawing Sheets

F I G. 2
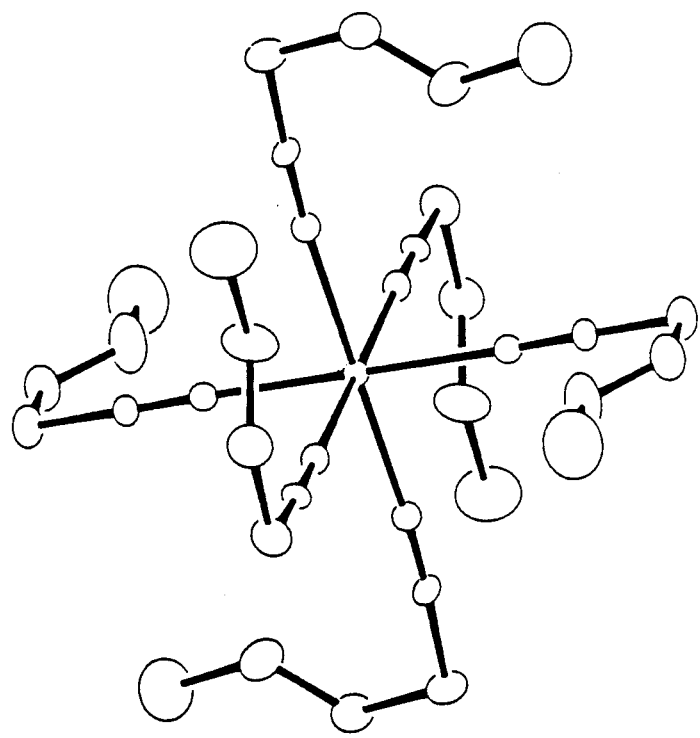

F I G. 3
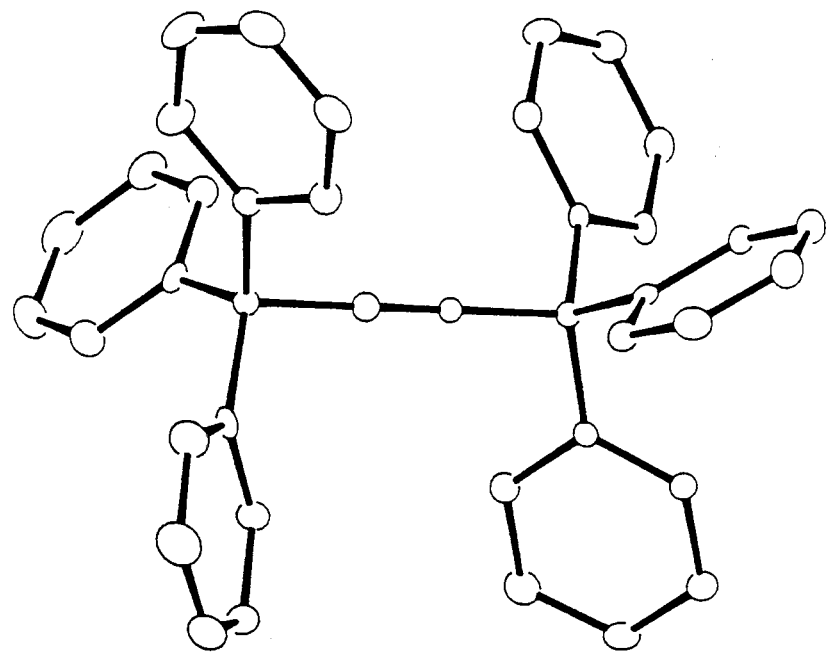

[HEXAKIS(PENTENENITRILO)NICKEL II]BIS-[μ-(CYANO) BIS(TRIPHENYLBORANE) (I)], ITS METHOD OF PREPARATION AND ITS USE

FIELD OF THE INVENTION

This invention relates to a chemical compound, namely [hexakis(pentenenitrilo)nickel II]bis[μ-(cyano)-bis(triphenylborane)(I)]. When the pentenenitrile is 3-pentenenitrile the compound has the formula $[Ni(CH_3CH=CHCH_2—CN)_6][\phi_3BCNB\phi_3]_2$, where $\phi$ is the phenyl radical. This compound can be prepared by the reaction of known nickel compounds with pentenenitrile. The compound is useful as a promoter in the preparation of adiponitrile by the hydrocyanation of 3 or 4-pentenenitrile.

BACKGROUND OF THE INVENTION

Cone U.S. Pat. No. 4,394,321 discloses the compound $Ni[NC(CH_2)_4CN]_2[NCB\phi_3]_2$, hereinafter referred to as NCBC. This compound may be reacted in pentenenitrile to produce the compound of this invention.

Various organo boron compounds have been employed in the prior art to promote the hydrocyanation of 3,4-pentenenitrile to adiponitrile—see, for example, Shook U.S. Pat. No. 4,082,811 where triarylborane is so employed, and the triarylborane recovered from the catalyst residue. The compound of this invention may be used in a manner like that taught in Shook to produce adiponitrile.

SUMMARY OF THE INVENTION

This invention is the chemical compound: [hexakis(-pentenenitrilo)nickel II]bis[μ-(cyano)bis(triphenylborane)(I)]; the method of preparation of the compound; and the use of the compound in the hydrocyanation of 3 or 4-pentenenitrile to form adiponitrile.

The compound of the invention consists of a cation $Ni(CH_3CH=CHCH_2CN)_6^{+2}$ and two anions $[\phi_3BCNB\phi_3]^{-1}$. The cation has perfect octahedral symmetry. The anion has a threefold axis passing through the two boron atoms and the carbon atoms attached to the nitrogen atom.

The compound of the invention may be prepared by heating NCBC in pentenenitrile to a temperature above about 50° C. The reaction steps are believed to be as follows:

(Step 1)
$Ni(NC(CH_2)_4CN)_2(NCB\phi_3)_2 + 4(CH_3CH=CHCH_2CN) \rightarrow Ni(CH_3CH=CHCH_2CN)_4(NCB\phi_3)_2 + 2NC(CH_2)_4CN$ (Step 2) $2Ni(CH_3CH=CHCH_2CN)_4(NCB\phi_3)_2 \rightarrow Ni(CH_3CH=CHCH_2CN)_6(\phi_3BCNB\phi_3)_2 + Ni(CN)_{2(Solid)}$.

The compound of the invention may also be prepared by reacting triphenylborane with solutions of pentenenitrile containing $Ni(CH_3CH=CHCH_2CN)_4(NCB\phi_3)_2$. Example 3 below shows the preparation by this process. The triphenylborane employed in this process can be that contained in the catalyst residue that results from the hydrocyanation of 3,4-pentenenitrile using triphenylborane as a promoter. The reaction proceeds even though the triphenylborane exists in the residue in a state that is no longer active as a promoter.

The compound of the invention can also be prepared by the reaction of triphenylborane, sodium cyanide, pentenenitrile, and nickel dichloride dimethoxyethane. Example 4 below illustrates this method of preparation.

The process for preparing the compound of the invention proceeds satisfactorily at atmospheric pressure and at temperatures between 50° and 200° C. The ingredients that react to form the compound may be present in approximately stoichiometric amounts; however, the reaction will proceed with different ratios of the ingredients, for example, with the pentenenitrile being present in a large excess.

The compound of the invention has the I.R. spectra shown in the FIG. 1, and the single crystal X-ray analysis shown in FIGS. 2 and 3, FIG. 2 depicting the cation, and FIG., 3 depicting the anion.

DETAILED DESCRIPTION OF THE INVENTION

Example 1

Preparation from NCBC

Figure 1:
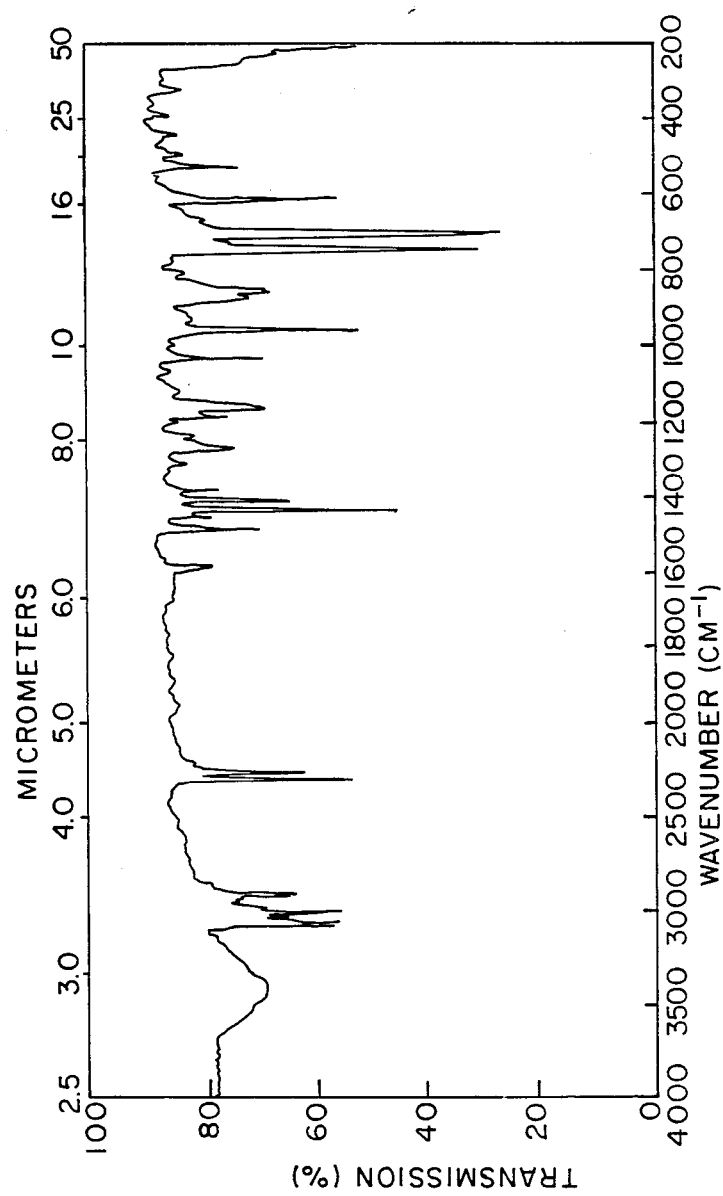

In a glass reaction vessel that contains a magnetic stirrer, 4.25 g of NCBC was mixed with sufficient 3-pentenenitrile to give 50 ml of slurry. The reactor was placed in a heat bath at 125° C., and the reaction allowed to proceed for 5 minutes after the temperature reached 120° C. The reactor was removed from the heat bath and placed in an ice bath to quench the reaction. The contents were then cooled to about 25° C. The contents were filtered to remove the black nickel-rich solid product, and a clear dark green product solution was isolated. The solution was placed in a refrigerator overnight, which caused solids to precipitate. Infrared analysis of the solids showed them to be the compound of the invention.

Example 2

Preparation of Large Crystals of Product for Analysis

In a glass reaction vessel that contains a magnetic stirrer, 2.125 g of NCBC was mixed with sufficient 3-pentenenitrile to give 50 ml of slurry. The reactor was placed in a heat bath at 125° C., and the reaction allowed to proceed for 5 minutes after the temperature reaches 120° C. The reactor was removed from the heat bath and placed in an ice bath to quench the reaction. The contents were cooled to 25° C. The contents were filtered to remove the black nickel-rich solids, and a dark green product solution was obtained. After standing for two weeks, large (~1 mm) cubic crystals formed which gave an infrared spectrum typical of $Ni(CH_3CH=CHCH_2CN)_6(\phi_3BNCB\phi_3)_2$.

These crystals were analyzed by X-ray diffraction to establish chemical structure, as shown in FIGS. 2 and 3.

Example 3

Preparation from $Ni(CH_3—CH=CH—CH_2—CN)_4(NCB\phi_3)_2$ and $\phi_3B$

A solution containing 1 g of $Ni(CH_3—CH=CH—CH_2—CN)_4(NCB\phi_3)_2$ dissolved in 9 g of 3-pentenenitrile was prepared. A second solution was prepared which contained 0.65 g of $\phi_3B$ dissolved in 9.35 g of 3-pentenenitrile. One gram of each solution was mixed together, which caused the immediate precipitation of a light purple solid. The solid was washed with cyclohexane and dried. An infrared scan of the solid showed it to be the compound of the invention.

Example 4

Direct Synthesis from φ₃B, NaCN, and NiCl₂.DME

A reaction was carried out by reacting 9.7 g of φ₃B, 1.0 g NaCN, and 50 g of 3-pentenenitrile. This mixture was heated to 60° C. for 1 hr with stirring. The mixture was then filtered, and 2.2 g of NiCl₂.DME (i.e., nickel dichloro dimethoxyethane) was added to the filtrate. The resulting mixture was heated to 100° C. and immediately filtered. The filtrate was allowed to cool to room temperature, which caused solid product to precipitate. Infrared analysis of the solid product showed it to be the product of the invention.

Example 5

Hydrocyanation Performance

A catalyst solution was prepared by dissolving 4.40 g of Ni[para-tolyl phosphite]₄ and 3.75 cc of paratolyl phosphite in 92 cc of 3-pentenenitrile under a nitrogen atmosphere. To a 10 cc aliquot of this catalyst solution was added 0.240 g of [hexakis(pentenenitrilo)nickel II]bis[μ-(cyano)bis(triphenylborane)(I)], which corresponds to 0.5 moles per mole of Ni[para-tolyl phosphite]₄. The mixture was heated in a thermostated oil bath to the desired reaction temperature. Hydrogen cyanide was added to the reaction mixture by passing nitrogen gas at 5 cc/min through liquid hydrogen cyanide at 0° C., and then to the reaction vessel just above the liquid level. The reactions were run until adiponitrile production ceased. Reactions were run at 40°, 51°, and 80° C., and the results are given in the following table.

| Temp (°C.) | 3-pentene- nitrile conv (%) | Yields (%) | | | |
|---|---|---|---|---|---|
| | | Adipo- nitrile | Methyl- glutaro- nitrile | Ethyl- succino- nitrile | 2-pentene nitrile |
| 40 | 31 | 92.8 | 3.1 | 0.3 | 3.9 |
| 51 | 35 | 90.3 | 3.3 | 0.3 | 6.0 |
| 80 | 29 | 75.5 | 3.8 | 0.4 | 20.3 |

In the above table, yield % of adiponitrile is defined by the equation:

$$\text{Yield \%} = \text{adiponitrile} \times 100/(\text{adiponitrile} + \text{methylgluteronitrile} + \text{ethylsuccinonitrile} + \text{2-pentenenitrile})$$

As a comparative, hydrocyanations were performed using 1 mole of φ₃B per mole of Ni[para-tolyl phosphite]₄, all other conditions being the same. The results for φ₃B promoter are as follows:

| Temp (°C.) | 3-pentene- nitrile conv (%) | Yields (%) | | | |
|---|---|---|---|---|---|
| | | Adipo- nitrile | Methyl- glutaro- nitrile | Ethyl- succino- nitrile | 2-pentene nitrile |
| 40 | 29 | 93.4 | 2.9 | 0.3 | 3.4 |
| 51 | 29 | 90.3 | 3.3 | 0.3 | 6.1 |
| 80 | 30 | 76.7 | 3.8 | 0.4 | 19.1 |

We claim:
1. [Hexakis(pentenenitrilo)nickel (II)]bis[μ-(cyano)bis(triphenylborane)(I)].
2. A process for the preparation of [hexakis(pentenenitrilo) nickel (II)]bis[μ-(cyano)bis(triphenylborane)(I)] which comprises reacting a mixture containing pentenenitrile and Ni(NC(CH₂)₄CN)₂(NCBφ₃)₂.
3. A process for the preparation [hexakis(pentenenitrilo)nickel(II)]bis[μ-(cyano)bis(triphenylborane)(I)] which comprises reacting a mixture containing pentenenitrile, triphenylborane and Ni(CH₃CH=CHCH₂CN)₄(NCBφ₃)₂.
4. A process for the preparation of [hexakis(pentenenitrile)nickel(II)]bis[μ-(cyano)bis(triphenylborane)(I)] which comprises reacting a mixture containing pentenenitrile, triphenylborane, sodium cyanide, and nickel dichlorodimethoxyethane.

* * * * *